(12) United States Patent
Korchia Maor

(10) Patent No.: US 11,344,567 B2
(45) Date of Patent: May 31, 2022

(54) METHODS OF TREATING CANCER USING PLATANOSIDE AND ISOMERS THEREOF

(71) Applicant: SHARE GAL RESEARCH AND DEVELOPMENT LTD, Bet El (IL)

(72) Inventor: Yehoshua Korchia Maor, Jerusalem (IL)

(73) Assignee: SHARE GAL RESEARCH AND DEVELOPMENT LTD, Bed El (IL)

(*) Notice: Subject to any disclaimer, the term of this patent is extended or adjusted under 35 U.S.C. 154(b) by 0 days.

(21) Appl. No.: 17/312,404

(22) PCT Filed: Dec. 9, 2019

(86) PCT No.: PCT/IL2019/051339
§ 371 (c)(1),
(2) Date: Jun. 10, 2021

(87) PCT Pub. No.: WO2020/121297
PCT Pub. Date: Jun. 18, 2020

(65) Prior Publication Data
US 2022/0040213 A1    Feb. 10, 2022

Related U.S. Application Data

(60) Provisional application No. 62/777,279, filed on Dec. 10, 2018.

(51) Int. Cl.
| | |
|---|---|
| *A61K 31/70* | (2006.01) |
| *A01N 43/04* | (2006.01) |
| *A61K 31/7048* | (2006.01) |
| *A61P 35/00* | (2006.01) |
| *A61K 36/17* | (2006.01) |

(52) U.S. Cl.
CPC .......... *A61K 31/7048* (2013.01); *A61K 36/17* (2013.01); *A61P 35/00* (2018.01)

(58) Field of Classification Search
None
See application file for complete search history.

(56) References Cited

PUBLICATIONS

Liu et al. "Treatment of liver cancer." Cold Spring Harbor perspectives in medicine 5.9 (2015): a021535.*
Bush et al. Neurosurg Rev (2017), vol. 40, pp. 1-14.*
Garrido-Laguna et al. Natural Reviews Clinical Oncology (2015), vol. 12, pp. 319-334.*
Anastasiadis, P. Z., et al. (2000). The p120 catenin family: complex roles in adhesion, signaling and cancer. Journal of Cell Science, 113(8), 1319-1334.
Ben-Arye, E., et al. (2016). Exploring an herbal "wonder cure" for cancer: a multidisciplinary approach. Journal of cancer research and clinical oncology, 142(7), 1499-1508.
Bishop, A. L., et al. (2000). Rho GTPases and their effector proteins. Biochemical Journal, 348(2), 241-255.
Dewick, P. M. (2009). Medicinal Natural Products: A Biosynthetic Approach, 3rd Edition.
Dimas, K., et al. (2000). Cytotoxic activity of kaempferol glycosides against human leukaemic cell lines in vitro. Pharmacological research, 41(1), 83-86.
Friedrich, J., et al. (2009). Spheroid-based drug screen: considerations and practical approach. Nature protocols, 4(3), 309.
Gorrini, C., et al. (2013). Modulation of oxidative stress as an anticancer strategy. Nature reviews Drug discovery, 12(12), 931-947.
Gupta, A., et al. (1999). Increased ROS levels contribute to elevated transcription factor and MAP kinase activities in malignantly progressed mouse keratinocyte cell lines. Carcinogenesis, 20(11), 2063-2073.
Hazard, L. (2009). The role of radiation therapy in pancreas cancer. Gastrointestinal cancer research: GCR, 3(1), 20-28.
Hensley, C. T., et al. (2013). Glutamine and cancer: cell biology, physiology, and clinical opportunities. The Journal of clinical investigation, 123(9), 3678-3684.
Ibragic, S., et al. (2015). Chemical composition of various Ephedra species. Bosnian journal of basic medical sciences, 15(3), 21.
Ibrahim, M. A., et al. (2009). Methicillin-resistant *Staphylococcus aureus* (MRSA)-active metabolites from *Platanus occidentalis* (American sycamore). Journal of natural products, 72(12), 2141-2144.
International Search Report and Written Opinion issued for PCT Application No. PCT/IL2019/051339 dated Mar. 12, 2020.
Jemal, A. (2003). Cancer Statistics, 2003. Ca Cancer J Clin, 53, 5-26.
Liberti, M. V., et al. (2016). The Warburg effect: how does it benefit cancer cells?. Trends in biochemical sciences, 41(3), 211-218.
Lillemoe, K. D., et al. (2000). Pancreatic cancer: state-of-the-art care. CA: a cancer journal for clinicians, 50(4), 241-268.
Liu, J., et al. (2015). Increased oxidative stress as a selective anticancer therapy. Oxidative medicine and cellular longevity, 2015.
Mendelovich, M., et al. (2017). Effect of Ephedra foeminea active compounds on cell viability and actin structures in cancer cell lines. Journal of Medicinal Plants Research, 11(43), 690-702.
Nam, N. H., et al. (2003). Antiinvasive, antiangiogenic and antitumour activity of Ephedra sinica extract. Phytotherapy Research: An International Journal Devoted to Pharmacological and Toxicological Evaluation of Natural Product Derivatives, 17(1), 70-76.
Nishanbaev, S. Z., et al. (2010). New oligomeric proanthocyanidin glycosides platanoside-A and platanoside-B from Platanus orientalis trunk bark. Chemistry of natural compounds, 46(3), 357-362.
Oshima, N., et al. (2016). Efficiently prepared ephedrine alkaloids-free Ephedra Herb extract: a putative marker and antiproliferative effects. Journal of natural medicines, 70(3), 554-562.

(Continued)

*Primary Examiner* — Patrick T Lewis
(74) *Attorney, Agent, or Firm* — Mark S. Cohen; Pearl, Cohen Zedek Latzer Baratz LLP

(57) ABSTRACT

This invention relates to methods of treating cancer with platanoside and/or isomers thereof or pharmaceutically acceptable salts thereof, particularly treatment of a pancreatic, liver or brain cancer. This invention further relates to methods of treating cancer with platanoside and/or isomers thereof, produced from *Ephedra foeminea*.

4 Claims, 4 Drawing Sheets

(56) References Cited

PUBLICATIONS

Ramachandran, V., et al. (2015). Glucose uptake through translocation and activation of GLUT4 in PI3K/Akt signaling pathway by asiatic acid in diabetic rats. Human & experimental toxicology, 34(9), 884-893.

Sosa, V., et al. (2013). Oxidative stress and cancer: an overview. Ageing research reviews, 12(1), 376-390.

Storz, P. (2005). Reactive oxygen species in tumor progression. Front Biosci, 10(1-3), 1881-1896.

Strobel, P., et al. (2005). Myricetin, quercetin and catechin-gallate inhibit glucose uptake in isolated rat adipocytes. Biochemical Journal, 386(3), 471-478.

Szatrowski, T. P., et al. (1991). Production of large amounts of hydrogen peroxide by human tumor cells. Cancer research, 51(3), 794-798.

\* cited by examiner

METHODS OF TREATING CANCER USING PLATANOSIDE AND ISOMERS THEREOF

FIELD OF THE INVENTION

This invention relates to methods of treating cancer with platanoside and/or isomers thereof or pharmaceutically acceptable salts thereof, particularly treatment of a pancreatic, liver or brain cancer. This invention further relates to methods of treating cancer with platanoside and/or isomers thereof, produced from *Ephedra foeminea*.

BACKGROUND OF THE INVENTION

Cancer is a major public health problem worldwide and is the second leading cause of death in the United States. Among the diversity of cancer types, pancreatic adenocarcinoma is one of the most lethal due to its rapid growth and propensity to invade adjacent organs and metastasize.

The treatments for cancer are usually one or more of surgery, radiation, and gene- or drug-based therapy. Nevertheless most of the available drugs today are not really cures, they merely slow down cancer growth, providing a few more months of life and many times with worse symptoms than the cancer itself. Moreover, these drugs and treatments are expensive, in many cases too expensive for many people to afford. Additionally, most cancer treatments are useful against a particular type of cancer.

Due to its rapid growth and prognostic to invade adjacent organs and metastasize pancreatic adenocarcinoma is considered one of the most lethal forms of cancer. The early stages of this cancer do not usually produce symptoms, so the disease is generally advanced when it is diagnosed (Lillemoe, K. D. et al.; Ca. Can. J. Clin. 2000, 50, 241-268). It is estimated that ninety-nine percent of patients with adenocarcinoma of the pancreas will die within 5 years of diagnosis (Jemal, A. et al.; Can. stat. 2003, 53, 5-26). Pancreatic cancer is the fourth leading cause of cancer-related death in the United States and is the seventh most common cause of death worldwide (Lillemoe, K. D. et al.; Ca. Can. J. Clin. 2000, 50, 241-268). Treatment for pancreatic cancer is rarely effective because surgical excision offers the only possibility for a cure, and fewer than 15% of patients are candidates for tumor resection at the time of diagnosis. Chemotherapy provides only a slight survival advantage over surgical resection alone, and radiation therapy has not been demonstrated to be beneficial (Hazard, L.; Gast. Can. Res., 2009, 3, 20-28). More effective treatments are needed to improve the prognosis of patients with pancreatic cancer.

*Ephedra* is a genus of gymnosperm shrubs which belongs to the family of Ephedracea with over 30 registered species. As the majority of the gymnosperm plants, instead of fruits, it has bisexual strobilus which serves as food for birds. The leaves are degenerated and located in a sort of reddish membranous sheath on the stem which is green all year round. The various species of *Ephedra* are widespread throughout many lands. However, they are found in more abundance in southern Europe, Middle West, central Asia and northern China.

A diversity of *Ephedra* species, especially *E. sinica*, have traditionally been used by the Chinese for a variety of medical purpose for at least 5000 years (Dewick, P. M.; 2009, Medicinal natural products, a biosynthetic approach, 3$^{rd}$ edition, Wiley). Last studies have revealed to have anti-invasive, antiangiogenic and antitumor activities of *Ephedra sinica* extract (Nam, N. H. et al.; Phytother. Res. 2003, 17, 70-76). Nevertheless, most of the plants from the *Ephedra* genus contains alkaloids as ephedrine (E) and pseudoephedrine (PE) which have been considered the primary pharmacologically active substances in *Ephedra*. These alkaloids are known to induce palpitation, hypertension, insomnia, dysuria, bronchodilation, and pronounced effects on the central nervous system (CNS) by binding to adrenergic receptors (Oshima, N. et al.; J. Nat. Med. 2016, 70, 554-562)). Therefore, the administration of drugs containing *Ephedra* to patients with cardiovascular-related diseases is severely contraindicated. According to the Food and Drug Administration (FDA) assessment in 2004, food supplements containing E-type alkaloids represent an unacceptable health risk, bearing in mind the conditions of use. Consequently, FDA banned all over the counter drugs containing ephedrine (Ibragic, S. et al.; Bosn. J. Basic. Med. Sci., 15).

Recently, a particular species of the genus *Ephedra*, namely *Ephedra foeminea*, drew attention and interest as a pharmaceutical agent mainly due to two reasons: a) Surprisingly, no ephedrine alkaloids were identified in its chemical profile composition (Ibragic, S. et al.; Bosn. J. Basic. Med. Sci., 15); and b) reports from patients diagnosed with different types of cancer that were supposedly healed from their ailments by drinking an infusion prepared with *Ephedra foeminea* stalks, seemingly in combination with conventional chemotherapy, and a report on reducing various cancerous cells' viability, such as lung, breast and colon cancer (Ben-Arye, E.; et al.; J. Cancer Res. Clin. Oncol. 2016, 142(7), 1499-1508; and Mendelovich, M. et al.; J. Med. Pla. Res. 2017, 11(43), 690-702, respectively).

It was found by the inventors that platanoside and platanoside structural isomers (i.e. where p-coumaric acid and kaempferol moieties are connected to the sugar in different positions than the original ones) are found in *Ephedra foeminea*. The inventors isolated and purified a fraction (F5c-1) from *Ephedra foeminea*, which contained >99.99% of platanoside and platanoside structural isomers.

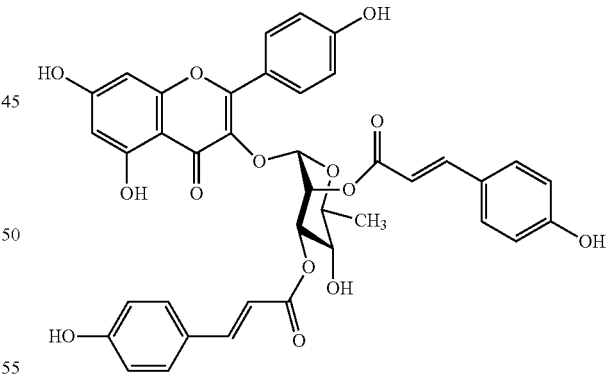

Platanoside

Platanoside was previously found to be active as an anti-leukemic agent and an anti-methicillin-resistant *Staphylococcus aureus* (Dimas, K. et al.; Pharm. Res. 2000, 41, 83-86; and Ibrahim, M. A. et al.; J. Nat. Prod. 2009, 72, 2141-2144, respectively). The inventors found, within the framework of this invention, that the F5c-1 fraction had the highest biological activity in pancreatic, liver or brain cancer treatment compared to other fractions isolated from *Ephedra foeminea*. It is denoted herein that compared to breast, lung or colon cancer cells viability which were shown to be reduced via treatment with *Ephedra foeminea* extractions/liquids (Mendelovich, M. et al.; J. Med. Pla. Res. 2017, 11(43), 690-702), it is much more difficult to treat pancreatic, liver or brain cancer. Similarly, treating leukemia with platanoside (Dimas, K. et al.; Pharm. Res. 2000, 41, 83-86) is not related to treatment of pancreatic, liver or brain cancer; the former concerns the blood system whereas the other ones are specific organs. Furthermore, pancreatic cancer is considered to be one of the most lethal forms of cancer (see above); and affecting brain cancer means passing the blood-brain barrier (BBB), an act which is not considered as straightforward. Thus, the treatment of pancreatic, liver or brain cancer is a long-lasting problem.

Accordingly, this invention provides uses of platanoside and isomers thereof in the treatment of cancer, especially their use in the treatment of pancreatic cancer.

SUMMARY OF THE INVENTION

In one aspect, this invention provides a method of treating a pancreatic, liver or brain cancer in a subject, comprising administering to the subject a therapeutically effective amount of platanoside and/or isomers thereof.

In one embodiment, the method comprises administering to the subject a therapeutically effective amount of platanoside and isomers thereof. In another embodiment, the platanoside and/or isomers thereof are extracted from *Ephedra foeminea*. In another embodiment, the administered platanoside and/or isomers thereof have a purity of >99.99%.

BRIEF DESCRIPTION OF THE DRAWINGS

The subject matter regarded as the invention is particularly pointed out and distinctly claimed 25 in the concluding portion of the specification. The invention, however, both as to organization and method of operation, together with objects, features, and advantages thereof, may best be understood by reference to the following detailed description when read with the accompanying drawings in which:

FIG. 1A: Representative micrographs before MTT assay; and FIG. 1B: MTT assay.

Figure 1A:
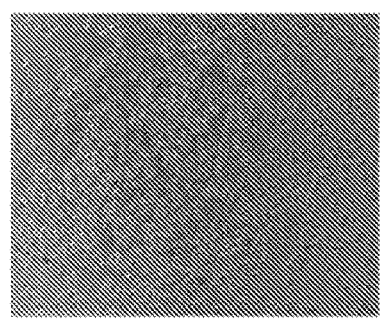
FIGS. 1A-1B depict morphology and viability evaluation of Aspc1 cells at the end point of the real time cytotoxic detection assay, 32 hours after treatment with fraction F5c-1.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

Uses of Platanoside and/or Isomer Thereof

In one aspect, this invention provides a method of treating a pancreatic, liver or brain cancer in a subject, comprising administering to the subject a therapeutically effective amount of platanoside and/or isomers thereof or pharmaceutically acceptable salts thereof. A platanoside isomer (or "structural isomer") is defined herein as having the p-coumaric acid and kaempferol moieties connected to the sugar in different positions than in platanoside itself.

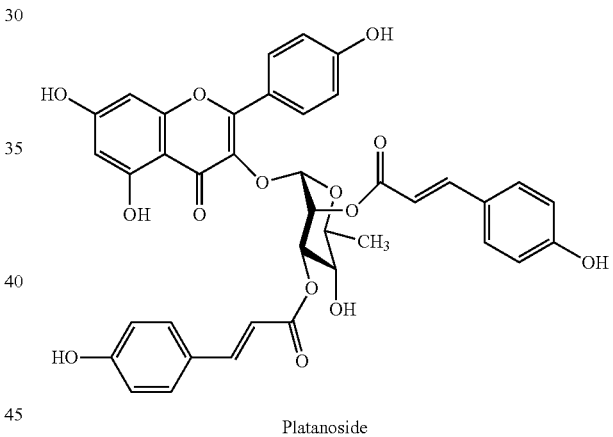

Platanoside

In one embodiment, the method comprises administering to the subject a therapeutically effective amount of platanoside or its isomers or pharmaceutically acceptable salts thereof. In one embodiment, the method comprises administering to the subject a therapeutically effective amount of platanoside and its isomers or pharmaceutically acceptable salts thereof. In one embodiment, the method comprises administering to the subject a therapeutically effective amount of platanoside. In another embodiment, the platanoside and/or isomers thereof are extracted from *Ephedra foeminea*. In another embodiment, the administered platanoside and/or its isomers or pharmaceutically acceptable salts thereof have a purity of >99.99%.

In another embodiment, the cancer is pancreatic cancer. In another embodiment, the cancer is liver cancer. In another embodiment, the cancer is brain cancer. In another embodiment, the disease is a hyper-proliferative and/or a neoplastic disease. In another embodiment, "treating" is alleviating a neoplastic or cancerous symptoms and/or disturbances. In another embodiment, "treating" is inhibiting tumor growth.

In another embodiment, "treating" is reducing tumor size. In another embodiment, "treating" is destroying the tumor. In another embodiment, "treating" is inhibiting malignancy. Each possibility represents a separate embodiment of this invention.

In one additional aspect, this invention provides platanoside and/or isomers thereof or pharmaceutically acceptable salts thereof to be used in the methods for treating a pancreatic, liver or brain cancer, as described above. In one embodiment, the compound(s) is used as a chemotherapeutic agent, targeted at a cancerous cell, a neoplastic cell, a malignant cell or any combination thereof. In another embodiment, the chemotherapeutic agent has low toxicity to non-malignant tissues. In another embodiment, the compound(s) has a chemotherapeutic effect. Each possibility represents a separate embodiment of this invention.

As used herein, subject or patient refers to any mammalian patient, including without limitation, humans and other primates, dogs, cats, horses, cows, sheep, pigs, rats, mice, and other rodents. In some embodiments, the subject is male. In some embodiments, the subject is female. Each possibility represents a separate embodiment of this invention. In some embodiments, while the methods as described herein may be useful for treating either males or females.

In another embodiment, the platanoside and/or its isomers or pharmaceutically acceptable salts thereof is/are administered systemically or, alternatively, administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. Each possibility represents a separate embodiment of this invention.

In some embodiments, the methods of this invention comprises administering platanoside and/or isomers thereof or pharmaceutically acceptable salts thereof in a weight percentage of about 0.01 to 99, preferably from about 20 to 75 percent, together with adjuvants, carriers, stabilizers and/or excipients. While individual needs may vary, determination of optimal ranges of effective amounts of each component is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the compounds administered by methods of this invention can also be determined readily by those with ordinary skill in art. That is, the frequency of administration and size of the dose can be established by routine optimization, preferably while minimizing any side effects. Each possibility represents a separate embodiment of this invention. In this regards, it is herein defined that "weight percentage" (e.g. 0.01-99%; see above) should not be confused with "purity" of platanoside and/or isomers thereof or pharmaceutically acceptable salts thereof (e.g. >99.99%): "weight percentage" refers to the weight % of platanoside and/or isomers thereof or pharmaceutically acceptable salts thereof within some composition to be administered which comprises as well adjuvants, carriers, stabilizers and/or excipients; and "purity" refers to the percentage (molar or weight) of platanoside and/or isomers thereof or pharmaceutically acceptable salts thereof, before provision of them within a pharmaceutical composition (e.g. their percentage of them following their extraction, isolation and purification from *Ephedra foeminea*; see Example 1).

In some embodiments, the pharmaceutical composition, used in the methods of this invention as described above, includes platanoside and/or isomers thereof or pharmaceutically acceptable salts thereof, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions. Each possibility represents a separate embodiment of this invention.

In one embodiment, the solid unit dosage forms can be of the conventional type. The solid form can be a capsule and the like, such as an ordinary gelatin type containing the active compounds administered via methods of this invention and a carrier, for example, lubricants and inert fillers such as, lactose, sucrose, or cornstarch. In some embodiments, these compounds are tabulated with conventional tablet bases such as lactose, sucrose, or cornstarch in combination with binders like acacia, cornstarch, or gelatin; disintegrating agents, such as cornstarch, potato starch, or alginic acid, and a lubricant, like stearic acid or magnesium stearate. Each possibility represents a separate embodiment of this invention.

In on embodiment, the tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil. Each possibility represents a separate embodiment of this invention.

In some other embodiments, various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor. Each possibility represents a separate embodiment of this invention.

In one embodiment, for oral therapeutic administration, the active compounds administered via methods of this invention can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage is obtained. Preferred compositions according to the methods of this invention are prepared so that an oral dosage unit contains between about 1 mg and 800 mg of active compound. Each possibility represents a separate embodiment of this invention.

In another embodiment, the active compounds administered via method of this invention may be orally administered, for example, with an inert diluent, or with an assimilable edible carrier, or they can be enclosed in hard or soft shell capsules, or they can be compressed into tablets, or they can be incorporated directly with the food of the diet. Each possibility represents a separate embodiment of this invention.

In some embodiments, the pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils. Each possibility represents a separate embodiment of this invention.

In some embodiments, the compounds or pharmaceutical compositions administered via methods of this invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Each possibility represents a separate embodiment of this invention.

In one embodiment, the active compounds administered via methods of this invention may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

In some embodiments, for use as aerosols, the active compounds administered via methods of this invention, in solution or suspension, may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In various embodiments, the compounds administered via methods of this invention are administered in combination with an anti-cancer agent. In various embodiments, the anti-cancer agent is a monoclonal antibody. In some embodiments, the monoclonal antibodies are used for diagnosis, monitoring, or treatment of cancer. In various embodiments, monoclonal antibodies react against specific antigens on cancer cells. In various embodiments, the monoclonal antibody acts as a cancer cell receptor antagonist. In various embodiments, monoclonal antibodies enhance the patient's immune response. In various embodiments, monoclonal antibodies act against cell growth factors, thus blocking cancer cell growth. In various embodiments, anti-cancer monoclonal antibodies are conjugated or linked to anti-cancer drugs, radioisotopes, other biologic response modifiers, other toxins, or a combination thereof. In various embodiments, anti-cancer monoclonal antibodies are conjugated or linked to a compound administered via methods of this invention.

In various embodiments, the compounds administered via methods of this invention are administered in combination with an agent treating Alzheimer's disease.

In various embodiments, the compounds administered via methods of this invention are administered in combination with an anti-viral agent.

In various embodiments, the compounds administered via methods of this invention are administered in combination with at least one of the following: chemotherapy, molecularly-targeted therapies, DNA damaging agents, hypoxia-inducing agents, or immunotherapy, each possibility represents a separate embodiment of this invention.

In some embodiments, platanoside and/or its isomers show strong biological activity by significant reducing viability of many different cancer cell lines where the human pancreatic Aspc1 cells present highly sensitive behavior. In one embodiment, in vitro results (see examples below, e.g. Example 5) show that F5c-1 is able to significantly change the expression pattern of key proteins in cancer metabolism such as GLUT-4 receptor and E-cadherin. GLUT-4 is responsible for the glucose uptake which was showed to be impaired in treated cells generating a significant stress response. E-cadherin upregulation impairs cancer cells migration and invasion of the surrounding tissues (i.e. metastasis).

The following examples are presented in order to more fully illustrate the preferred embodiments of the invention. They should in no way, however, be construed as limiting the broad scope of the invention.

EXAMPLES

Example 1

Extraction of Platanoside and/or Isomers Thereof (F5c-1) from *Ephedra foeminea* and Anti-Cancer Activity Initially, aqueous fraction of *Ephedra foeminea* stalks was solvent partitioned using liquid-liquid extraction (LLE) with Diethyl Ether (DEE). HPLC run of the DEE fraction showed several constituents. Thus, an alternative method of purification was developed to arrive at purer compounds. Indeed, methanol extraction of powdered *Ephedra foeminea* stalks gave rise to pure (>99.99%) three related compounds, i.e. fraction F5c-1 which consisted only of platanoside and isomers thereof. Such compounds showed the highest biological activity (reducing cancerous Asp1 cells viability to about 50% of initial value) compared to other components within *Ephedra foeminea*.

Example 2

General Methods and Techniques

Experimental Protocols of Cell Culture and Treatment

Adherent Human carcinoma cell lines were cultured according to standard mammalian tissue culture protocols and sterile technique. Caco2, HepG2, MCF-7 cell lines were cultured in high glucose Dulbecco's Modified Eagle Medium, HT29 cells were cultured in McCoy's 5A medium, Aspc1, A549, Mia Paca, U87MG and T98MG cells line were cultured in RPMI medium 1640 and HFF was culture in BIOAMF media. All media was supplemented with 10% fetal bovine serum, streptomycin (100 mg/ml), penicillin (100 U/ml) and Nystatin (12.5 U/ml). Cells were incubated in 5% $CO_2$ at 37° C. All tissue culture were maintained in 25 $cm^2$Nunc™ cell culture treated EasYFlask™ (ThermoFisher scientific) and all the media and supplements were obtained from Biological Industries. Treatment were performed by plating cells in a Nunc™ 96 micro well delta surface plates (ThermoFisher scientific) in a starting confluence of $1\times10^4$ cells/well. After 24 h of incubation, the compound of interest was added in different concentrations as shown in the presented results.

MTT Assay

Viability of the cells following treatment was determined using a commercially available MTT assay kit (ABCAM, ab146345) and performed according to manufacturer's instructions. Briefly, cells were seeded in a 96-well plate at a density of $1\times10^4$ cells/well (n=4). After overnight plating, cells were exposed to varying concentrations of the tested compounds (50-500 μM). Then, plates were incubated in a humidified atmosphere containing 5% $CO_{2+}$ in air at 37° C. for 24 hours. According to the MTT standard protocol, after 24, 48 or 72 h treatment, the media was removed and all cells were incubated with serum-free media containing 0.5 mg/ml MTT for 4 hours in the incubator. The MTT purple crystals formed by the viable cells were diluted using isopropanol containing 0.04 mol/L HCl. The quantification was determined by measuring the optical density at 570 nm in an enzyme-linked immunosorbent assay (Spark, Tecan) reader. Data was presented as proportional viability (%) by comparing the group treated with the tested compounds with the untreated cells, the viability of which is assumed to be 100%.

Spheroids Assembly and Viability

The spheroid formation potential of HT29 human colon cancer cell line was evaluated in 3D nonadherent culture condition. Initially the HT29 human cells were grown as a monolayer after which they were counted, re-suspended and plated with 1,500 cells per well in a 96-well plate pre-coated with a thin layer of 1.5% agarose (w/v) in McCoy's 5A medium containing 10% FBS and incubated at 37° C. in a humidified atmosphere of 5% CO2. Cell culture media was replaced every 2-3 days with fresh medium to remove cellular debris and the spheroids that were not well-formed. After the beginning of the multicellular tumor spheroid formation, the tested compounds were added at various concentrations (0.2, 0.4 and 0.6 mg/ml) and incubated for 24, 48 and 72 h. The number and diameter of colonies within each well were photographed and counted every day under the microscope (Olympus BX-51; Olympus, Hamburg, Germany), and the images of the representative fields were captured. Each sample was analyzed in triplicate, and all the experiments were performed three times. The viability of cells growing on the spheroids was measured by the APH (acid phosphatase) assay, which was performed according to manufacturer's instructions.

Protein Extraction and Western Blot Analysis

Whole cell lysate was prepared by washing cells pellets with 1× Phosphate buffer saline (Biological Industries), resuspending it in ice cold T lysis buffer [50 mM Tris-Cl (pH 7.5), 150 mM NaCl, 1 mM EDTA, 1% Triton X and 1× Halt™ protease and phosphatase inhibitor cocktail] and incubating for 30 minutes in ice. The lysate was centrifuged at 13,800 g for 10 min at 4° C. to clear the cellular debris. Total protein was quantified using the Bradford protein assay kit (Biorad, Hercules, Calif.). Equal amount of protein was resolved on precast Bolt™ 4-12% Bis-Tris Plus polyacrylamide gel (Invitrogen), electro-transferred to precast nitrocellulose stacks using iBlot®2 system (Invitrogen) and western blot analysis was performed using the antibodies described above. Immuno-detection was performed by blocking the membranes for 1 h in TNT buffer [10 mM Tris-Cl(pH 7.5), 150 mM NaCl, 0.05% Tween-20] containing 5% powdered non-fat milk followed by addition of the primary antibody (as indicated) in TNT for 2 h at room temperature. Specifically bound primary antibodies were detected with peroxidase-coupled secondary antibodies and developed by enhanced chemiluminescence (Biological Industries) according to manufacturer's instructions and quantitated using ImageQaunt LAS 4000 mini, General Electric). All experiments were performed at least three-five times using independent biological replicates.

Quantitative Real-Time PCR

Quantitative polymerase chain reaction (PCR) was carried out using the ABI 7700 instrument from Applied Biosystems, according to the manufacturer's instructions. Human PPARγ Taqman probe and primers (cat #Hs01115513_m1), human GAPDH Taqman probe and primers (cat #Hs99999905_m1) and human GLUT-4 taqman probe and primers (cat #Hs00168966_m1) were purchased from Applied Biosystems. Briefly, the reaction conditions consisted of 3 μl of cDNA and 1× Taqman assay primers in a final volume of 20 μl of supermix. The cycle conditions for real-time PCR were 95° C. for 10 min, followed by 40 cycles of 95° C. for 15 sec, and 60° C. for 1 min. The experiment was performed by three independent experiments with triplicate.

Immunoblot Analysis

Immunoblot analysis was performed using antibodies against GAPDH (1:6000 dilution; ab128915, Abcam), E-cadherin (1:10000 dilution; ab40772, Abcam), GLUT-4 (1:1000 dilution; G4048, SIGMA), and then species-specific HRP-labeled secondary antibodies were added. The blots were visualized using enhanced chemiluminescence (biological industries) and quantitated using ImageQaunt LAS 4000 mini, General Electric).

Subcutaneous Tumor Implantation

All the experiments were performed under strict compliance and regulations. $3-4\times10^6$ AsPC-1, A549 and T98G cells in 1:1:18 mixture of Methanol, Tween® 20 and saline were implanted in right and left flank of mice respectively. Once tumor volume was around 0.25 $cm^2$, mice were randomly divided into two groups with 4 mice in each group. Group I served as control and received the vehicle only whereas Group II received 30 mg/kg of the tested compounds by peritoneal (i.p) injection. Tumor area was measured twice a week until day 24. At day 24, mice were humanely sacrificed, and tumors were removed aseptically. Solid tumors were harvested in buffered formalin for further molecular and histological analyses.

2-DG Uptake Assay

After treatment with the tested compounds, cells were starved in low-glucose DMEM (Dulbecco's Modified Eagle Medium) with 0.5% serum for 16 h; cells were washed twice with 37° C. Krebs-Ringer phosphate (KRP) buffer (pH 7.4) (128 mM NaCl, 4.7 mM KCl, 1.65 mM $CaCl_2$, 2.5 mM $MgSO_4$, and 5 mM $Na_2HPO_4$). Glucose uptake was started by addition of 1 mM 2-deoxy-D-glucose (2-DG) for an additional 20 min at 37° C. Cells were gently washed three times with ice-cold DPBS and lysed. Sample was assayed using the Colorimetric Glucose Uptake Assay kit from Abcam (Cambridge, United Kingdom). Measurements were performed at least three replicates and then averaged.

Cell Viability

Tested compounds were evaluated for their ability to influence on cell viability and proliferation. A broad screening was performed using ten different cell lines as described in table 1, and four different concentrations were used (37.5, 75, 150 and 300 µM) to treat cells for 24 hours and determine the proliferation inhibitory profile of each novel chemical entity.

Example 3

Assessment of Cell Viability Following Treatment with F5c-1

TABLE 1 viability of cells treated with F5c-1

| Cell line | Molecule F5c(1) |
|---|---|
| A549 | 26% |
| Aspc1 | 21% |
| Mia Paca | 32% |
| HepG2 | 29% |
| T98G | 23% |
| MCF-7 | 20% |
| HT-29 | 39% |
| HFF | 70% |
| U87MG | 27% |
| CaCo2 | 71% |

Emphasized, underlined boxes represent viability values under 70%.

150 µM of F5c-1 showed high toxicity to all cell lines except normal fibroblasts (HFF) and colorectal (CaCo-2) cell lines (Table 1). This toxic effect also persisted with small concentrations of F5c-1 (37.5 µM) (not shown).

Example 4

A Real Time Cytotoxicity Detection Assay of Aspc1 Treated with Fraction F5c-1

To better evaluate the anticancer effect, a real time cytotoxicity detection assay was performed during the course of 72 hours on Aspc1 cells after treatment with fraction F5c-1. Aspc1 cells treated with F5c-1 for 24 hours at various doses (18-300 µM) results in a significant decrease on cell viability in a time and dose-dependent manner, nonetheless, apoptotic bodies were not identified by microscopy analysis (FIG. 1A), indicating that probably treated cells are inducing cell cycle arrest and stopping proliferation instead of inducing death by apoptosis.

Figure 2:
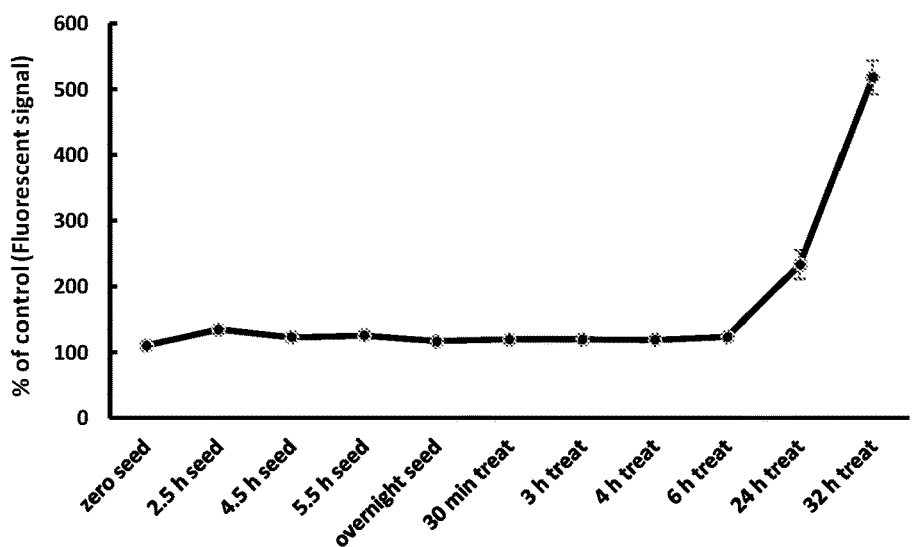
FIG. 2 depicts real time cytotoxicity detection assay during the course of 72 hours on Aspc1 cells treated with 300 µM of fraction F5c-1. Measurement of fluorescent signal was calculated from the percentage of the control.

Aspc1 cells were incubated with a non-toxic dye that binds to the DNA of died or damage cells. After 24 hours of incubation, cells were treated with fraction F5c-1. Cells treated with F5c-1 showed a significant effect achieving a maximum cell death after 32 hours from treatment (FIG. 2).

Figure 1B:
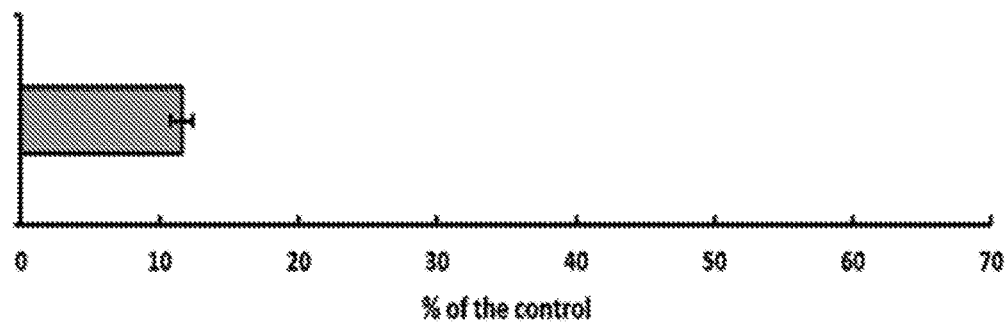

MTT viability assay was performed with the cells at the end point of the real-time cytotoxic detection assay in order to confirm the results (FIG. 1B). The level of the fluorescence signal was correlated with the viability level.

Example 5

Protein Expression Patterns in GLUT-4 Receptor and E-Cadherin

Chemical structure of the F5c-1 revealed strong similarity to the known flavonoids quercetin and kaempferol. It has been suggested that a transport inhibition mechanism in which flavonoids and GLUT4 (glucose transporter) interact directly, rather than by a mechanism related to protein-tyrosine kinase and insulin signaling inhibition (Strobel, P.; et al.; Biochem. J. 2005, 386, 471-478). This direct interaction of flavonoids with GLUT4 occurs at the same residues as glucose, thus inhibiting the glucose uptake into the cells. In F5c-1 GLUT-4 expression was upregulated.

The small GTPases of the RHO subfamily (Rho, Rac, and Cdc42) are signaling molecules that are primarily involved in several critical cellular processes, including cell proliferation, motility, and invasion (Bishop, L. A. et al.; Biochem. J. 2000. 348 part 2, 241-255). Recent reports revealed that the activity of RHO protein could be modulated by a functional interaction with catenin p120, which is found in cytosolic pools. Moreover, it was demonstrated that cadherins could titrate out p120 molecules from the cytosol, reducing their ability to affect RHO signaling (Anastasiadis, P. Z. et al. J. Cell Sci. 2000, 113 pt. 8, 1319-1334). Treating Aspc1 with F5c-1 resulted in similar results compared to GLUT-4 expression, regarding the expression pattern of E-cadherin, i.e. a significant upregulation, following in comparison to control cells was observed.

The result show that incubation of Aspc1 cells with F5c-1 for 24 h generated a significant increase in E-cadherin expression. Therefore, it is inferred that this upregulation may impair Aspc1 cancer cell invasion and migration by preventing the interaction between p120 and RHO proteins.

Example 6

Glucose Withdraw

Adapted cellular metabolism is a key feature found in cancer cells. Among different metabolic modifications showed by different tumor cells, aerobic glycolysis has been extensively studied as it represents a drastic change in the primary routes of non-cancerous cell metabolism. Thus, a common feature is that tumor cells preferentially transform glucose to lactate even in the presence of sufficient amounts of oxygen. This phenomenon is known as Warburg effect (Liberti., M. V. et al.; Trends. Biochem. Sci. 2016, 211-218).

As a consequence of this effect, cancer cells become heavily dependent on both glycolysis and glucose uptake. To incorporate sufficient amounts of glucose, cancer cells increase the expression of different glucose transporters known as GLUTs. Glucose transporter 4 (GLUT4) is mainly expressed in adipose tissue and skeletal muscle, but it has also been identified in other tissues including brain and breast. Its activation is dependent on insulin secretion and takes place mainly through the activation of the PI3K/AKT pathway (Ramachandran, V. et al.; Hum. Exp. Toxicol. 2015, 34, 884-893).

In this study, Aspc1 cells were pretreated with F5c-1 for 20, 40 and 80 minutes before adding a labeled 2-DG (2-deoxy-D-glucose) and measuring in a spectrophotometer. In all the incubation times a clear reduction was observed in the amount of the glucose analog signal inside the cells in comparison with controls cells (FIG. 3).

Figure 3:
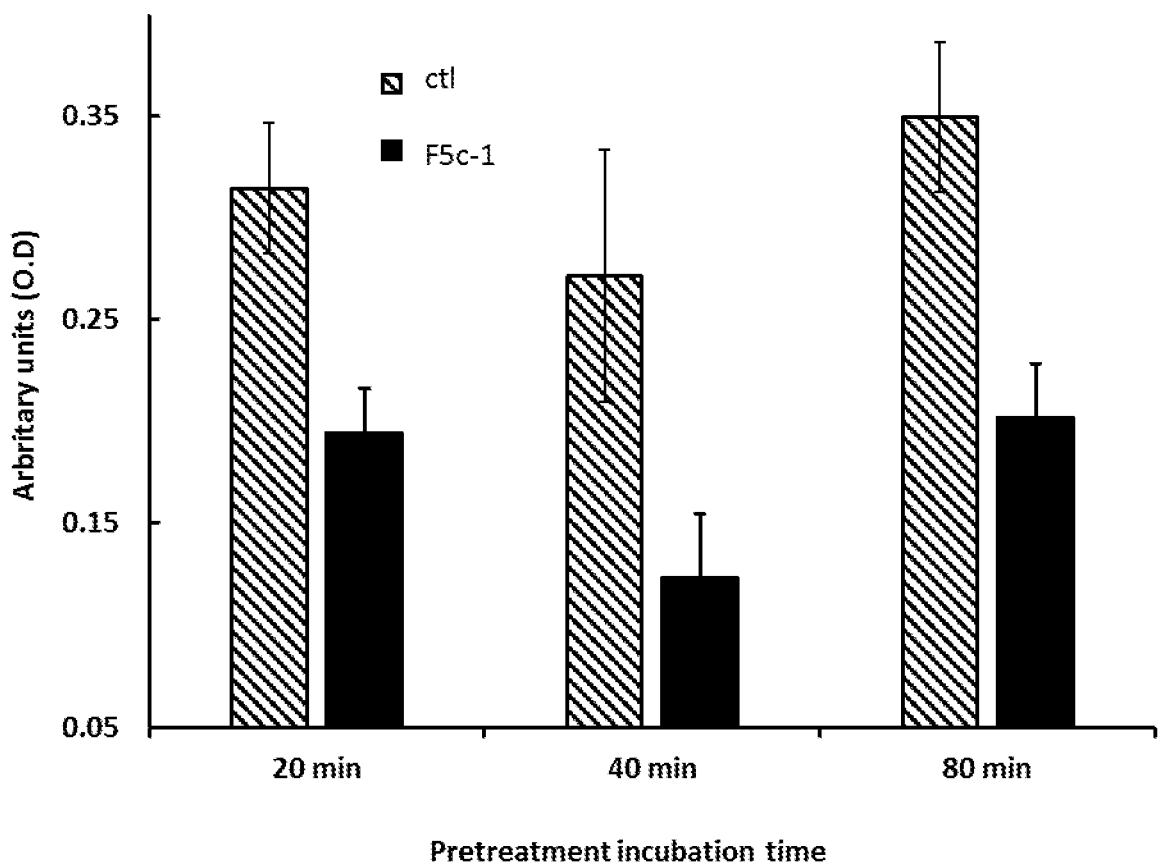
FIG. 3 depicts labelled 2-DG (2-deoxy-D-glucose) uptake in Aspc1 cells pretreated with F5c-1. F5c-1: solid fill, control: diagonal lines. Presented time is before treating with 2-DG.

It was shown that natural F5c-1 significantly impair glucose uptake (FIG. 3). Therefore the final result is a glucose withdrawal which generates significant stress responses affecting general cell metabolism, proliferation and other tumorigenic processes (Hensley, C. T. et al.; J. Clin. Invest. 2013, 123, 3678-3684). The consequence of this stress-response is a state of senescence, in which cells undergo a permanent proliferation and migration arrest accompanied by a set of functional and morphological changes (Ben Porath, I. et al.; J. Clin. Invest. 2004, 113, 8-13). Results of changes in the expression pattern of the glucose transporter together with glucose uptake impairment suggest the glucose metabolism as the key target pathway in the action of F5c-1. Further, these results are in concomitance with the generation of ROS and with the antiproliferative cytotoxic pattern as elucidated herein in other examples (e.g. Examples 7 and 4).

Example 7

Oxidative Stress Induction

Seeking to understand the mechanism of action by which F5c-1 is significantly reducing cancer cell viability as demonstrated above, it was further evaluated whether reactive oxygen species (ROS) accumulation may also be a pathway involved in the anticancer effect of F5c-1, as cancer cells may be more sensitive than normal cells to the accumulation of ROS.

Several characters of cancer cell behavior have been reported to be affected by oxidative stress-mediated signaling events (Sztarowski, T. P. et al.; Cancer Res. 1991, 51, 794-798; Storz, P.; Front. Biosci. 2005, 10, 1881-1896; and Gupta, A. et al.; Carcinogenesis 1999, 20, 2063-2073). For instance, ROS in cancer are involved in cell cycle progression and proliferation, cell survival and apoptosis, energy metabolism, cell morphology, cell-cell adhesion, cell motility, angiogenesis and maintenance of tumor stemness. Despite the elevated level of antioxidant defense mechanism in cancer cells, ROS levels are still higher than those observed in normal cells. Therefore, cancer cells may be more sensitive than normal cells to the accumulation of ROS, which offers an interesting therapeutic window (Liu, J. et al.; Oxid. Med. Cell. Longev. 2015, 294303). Targeting the enhanced antioxidant mechanisms and directly increasing ROS to reach a threshold that is incompatible with cell viability can selectively kill cancer cells, without affecting normal cells (Sosa, V. et al.; Ageing Res. Rev. 2013, 12, 376-390; and Gorrini, C. et al; Nat. Rev. drug Discov. 2013, 12, 931-947).

In this study, cells were co-treated with F5c-1 and dichlorofluorescin (DCFH), an organic dye that is easily oxidized to the fluorescent dichlorofluorescein (DCF) by oxidative species inside the cells. Oxidative stress was determined by direct measuring of the fluorescence intensity generated by DCF.

Figure 4:
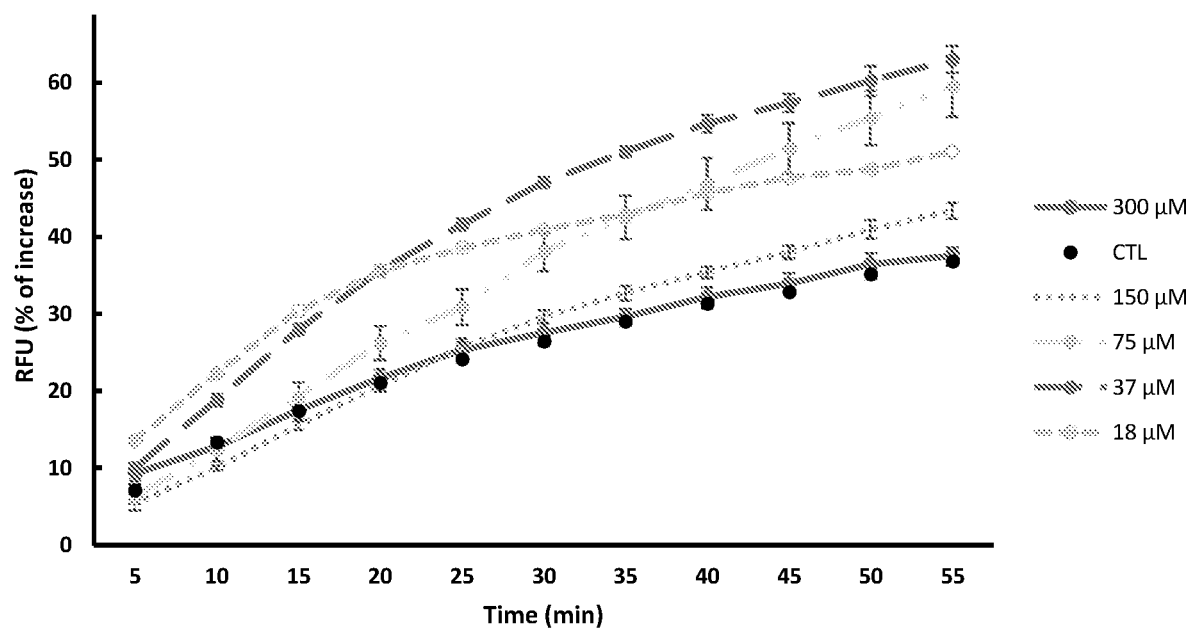
FIG. 4 depicts ROS formation in Aspc1 cells treated with F5c-1. Aspc1 cells were co-treated with F5c-1 and Dichlorofluorescin (DCFH). Fluorescence intensity of Dichlorofluorescein (DCF) was measured in 24 hours. Short line dashed, light grey—18 µM; long line dashed, dark grey—37 µM; dotted and lines dashed, light grey—75 µM; dotted dashed, grey—150 µM; solid dark grey line—300 µM; and black points—control.

Aspc1 cells co-treated with F5c-1 and DCFH for 24 hours that low concentrations (75, 37, 18 µM) were capable of increasing ROS whereas high concentrations (300 and 150 µM) behaved like control cells (FIG. 4).

F5c-1 demonstrated that treated cells reached the apex in cytotoxic levels 32 hours after treatment (Example 4, FIG. 2). Cell viability was reduced to about 10% (Example 4, FIG. 1B). The aggressive cytotoxic pattern observed in cells treated with 300 µM of F5c-1 could be the reason why low amount of ROS was generated in high concentrations (300 and 150 µM) (FIG. 4).

Example 8

Inhibition of Tumor Growth in 3D Spheroids

Figure 5:
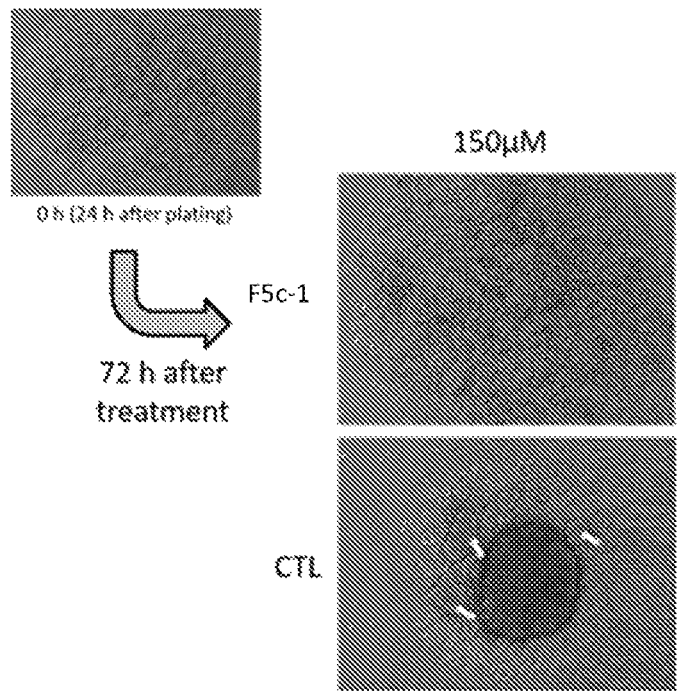
FIG. 5 depicts effect of F5c-1 on tumor formation. Treatment with F5c-1 started 24 hours after cells seeding (before tumor formation) and persisted for 72 hours. White arrows indicate examples of secondary tumor formation.

The cellular assays described above were performed in a monolayer system. Although monolayer systems partially reflect the microenvironment of cancer cells, there are currently more advanced culture methods that mimic in a better way the cellular interactions by the cells comprising the tumor (Freidrich, J. et. al.; Nat. Prot. 2009, 4, 309-324). Seeking to elucidate whether F5c-1 would also be able to hinder the growth of cancer cells, it was decided to proceed with assays in a 3D cell spheroid model. This assay can be applied to test whether the compounds treatment is able of impairing tumors formation or alternately to test the effect of the treatment in growing tumors. HT-29 cell line was used for this model due to its capacity to form spheroids in vitro. As can be seen, single dose (150 µM) treatment of F5c-1 impaired tumor formation (FIG. 5).

Figure 6:
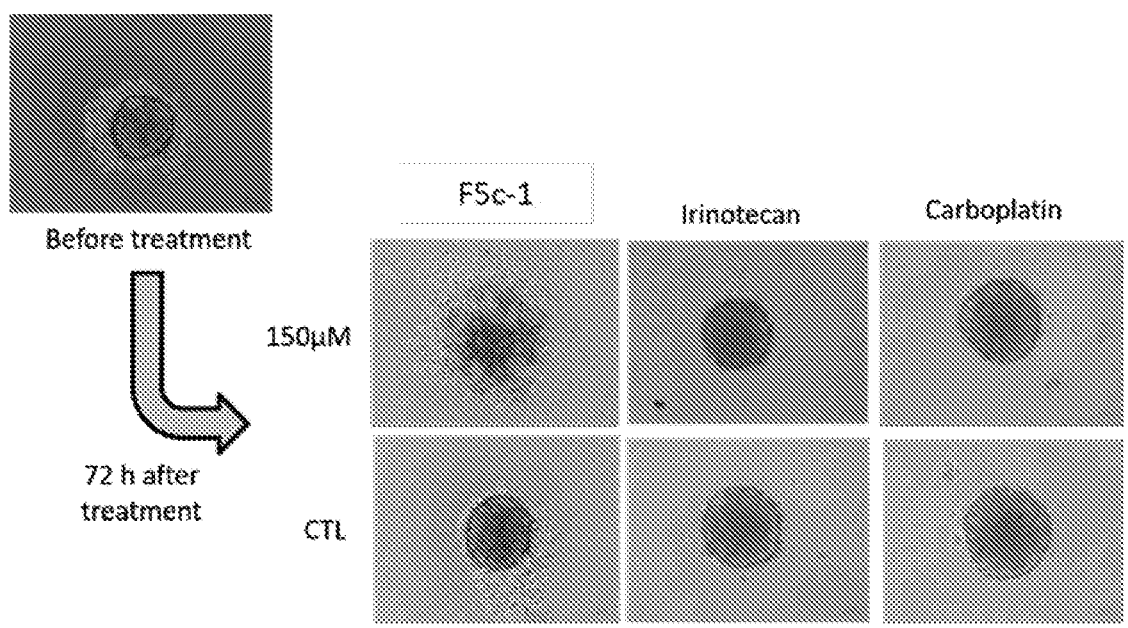
FIG. 6 depicts effect of F5c-1, irinotectan or carboplatin on tumor formation. Treatment with F5c-1, irinotectan or carboplatin started 72 hours after cells seeding (after spheroid formation) and persisted for additional 72 hours. Black dots represent necrotic areas.
Figure 7:
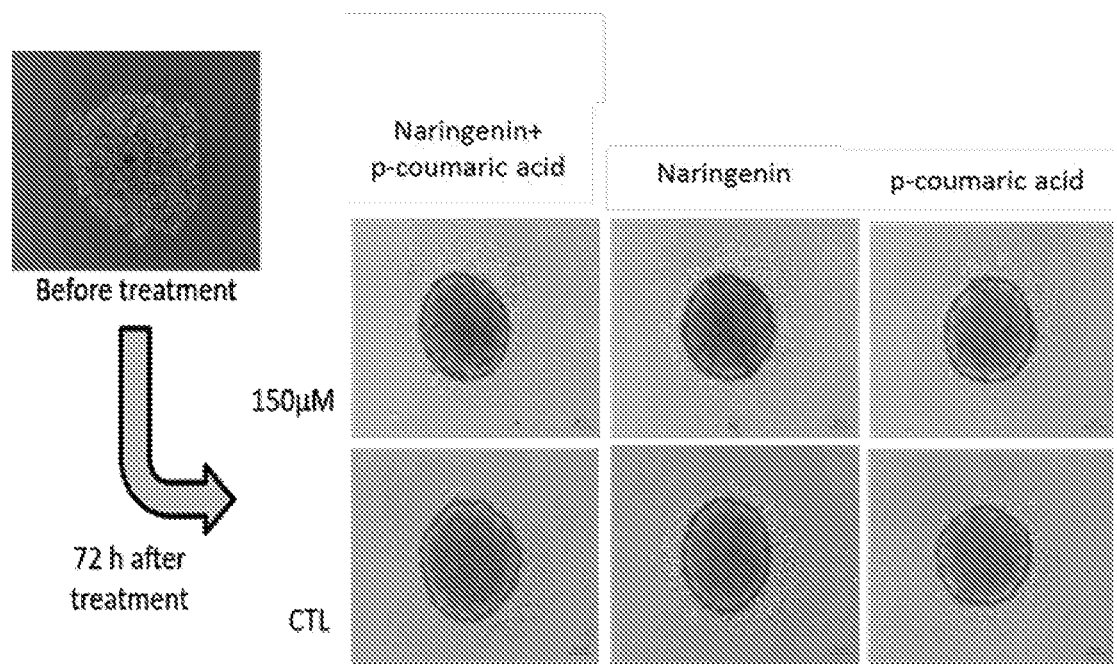
FIG. 7 depicts effect of naringenin and p-coumaric acid on tumor formation. Treatment with naringenin and p-coumaric acid started 24 hours after cells seeding (before tumor formation) and persisted for 72 hours. Black dots represent necrotic areas.

Growing tumors were also affected when a single dose of F5c-1 was applied 72 h after cells seeding (after spheroid formation), as such treatment impaired tumor formation as well (FIG. 6). In this regards, it should be mentioned that treatment using chemotherapeutic agents like irinotecan and carboplatin didn't generate any effect in tumor development (FIG. 6). Further, no effect was observed when spheroids were treated with the molecule backbones namely naringenin and p-coumaric acid (FIG. 7), indicating that the pharmacological activity is not caused by the moieties separately but by F5c-1 itself, through interaction with specific molecular targets in the tumor.

What is claimed is:

1. A method of treating a pancreatic, liver or brain cancer in a subject, comprising administering to the subject a therapeutically effective amount of platanoside and/or isomers thereof or pharmaceutically acceptable salts thereof.

2. The method of claim 1, wherein said method comprises administering to the subject a therapeutically effective amount of platanoside and isomers thereof or pharmaceutically acceptable salts thereof.

3. The method of claim 1 or 2, wherein said platanoside and/or isomers thereof are produced from *Ephedra foeminea*.

4. The method of claim 1, wherein said administered platanoside and/or isomers thereof or pharmaceutically acceptable salts thereof have a purity of >99.99%.

* * * * *